(12) United States Patent
Madsen

(10) Patent No.: US 9,649,448 B2
(45) Date of Patent: May 16, 2017

(54) ROTARY SENSOR MODULE WITH RESYNCHRONIZATION FEATURE

(71) Applicant: Novo Nordisk A/S, Bagsvaerd (DK)

(72) Inventor: John Oestergaard Madsen, Roedovre (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/037,602

(22) PCT Filed: Nov. 20, 2014

(86) PCT No.: PCT/EP2014/075180
§ 371 (c)(1),
(2) Date: May 18, 2016

(87) PCT Pub. No.: WO2015/075135
PCT Pub. Date: May 28, 2015

(65) Prior Publication Data
US 2016/0287808 A1 Oct. 6, 2016

Related U.S. Application Data

(60) Provisional application No. 61/908,465, filed on Nov. 25, 2013.

(30) Foreign Application Priority Data

Nov. 21, 2013 (EP) ..................................... 13193883

(51) Int. Cl.
*A61M 5/00* (2006.01)
*A61M 5/315* (2006.01)
(Continued)

(52) U.S. Cl.
CPC .......... *A61M 5/31568* (2013.01); *A61M 5/20* (2013.01); *A61M 5/24* (2013.01);
(Continued)

(58) Field of Classification Search
USPC ......................................... 604/111, 194, 200
See application file for complete search history.

(56) References Cited

U.S. PATENT DOCUMENTS 4,807,248 A 2/1989 Pyatt et al.
4,854,324 A 8/1989 Hirschman et al.
(Continued)

FOREIGN PATENT DOCUMENTS

EP 1198811 A1 4/2002
EP 2060284 A1 5/2009
(Continued)

*Primary Examiner* — Ahshik Kim
(74) *Attorney, Agent, or Firm* — Wesley Nicolas

(57) ABSTRACT

Drug delivery device comprising expelling means allowing a user to set a dose corresponding to a number of increments from an initial state, an indication member adapted to rotate in a first direction corresponding to the set dose, and rotate in an opposed second direction corresponding to an expelled dose, the indication member having an initial rotational position corresponding to both the initial state and the fully expelled dose state. Sensor means having an incremental counter synchronized with the rotational position of the indication member and having a reference point corresponding to the initial rotational position of the indication member. After detecting an error state the sensor means is adapted to re-synchronize by detecting the number of rotational increments for a set dose and for a subsequent expelled dose. If the numbers are identical the reference point is reset corresponding to the current rotational position of the indication member.

13 Claims, 9 Drawing Sheets

(51) Int. Cl.
  *G01D 5/25* (2006.01)
  *A61M 5/20* (2006.01)
  *G06F 19/00* (2011.01)
  *G01D 5/165* (2006.01)
  *A61M 5/31* (2006.01)
  *A61M 5/24* (2006.01)

(52) U.S. Cl.
  CPC ............ *A61M 5/31* (2013.01); *A61M 5/3155* (2013.01); *A61M 5/31553* (2013.01); *G01D 5/25* (2013.01); *G06F 19/3456* (2013.01); *A61M 5/31583* (2013.01); *A61M 2005/2411* (2013.01); *A61M 2005/3126* (2013.01); *A61M 2205/3317* (2013.01); *A61M 2205/50* (2013.01); *A61M 2205/52* (2013.01); *A61M 2205/702* (2013.01); *G01D 5/1655* (2013.01)

(56) References Cited

U.S. PATENT DOCUMENTS

| | | | |
|---|---|---|---|
| 4,891,476 | A | 1/1990 | Nation et al. |
| 5,315,077 | A | 5/1994 | Simon et al. |
| 5,669,489 | A | 9/1997 | von Ende |
| 5,739,775 | A | 4/1998 | Brandestini |
| 5,847,335 | A | 12/1998 | Sugahara et al. |
| 5,951,398 | A | 9/1999 | Yamamoto et al. |
| 7,008,399 | B2 | 3/2006 | Larsen et al. |
| 7,138,806 | B2 | 11/2006 | Gafner et al. |
| 7,635,817 | B2 | 12/2009 | Asada |
| 8,221,356 | B2 | 7/2012 | Enggaard et al. |
| 2005/0115317 | A1 | 6/2005 | Fouquet |
| 2008/0033369 | A1 | 2/2008 | Kohlbrenner et al. |
| 2008/0135090 | A1 | 6/2008 | Corrales |
| 2009/0318865 | A1 | 12/2009 | Moller et al. |
| 2010/0145656 | A1 | 6/2010 | Koehler et al. |
| 2011/0313349 | A1 | 12/2011 | Krulevitch et al. |
| 2011/0313395 | A1 | 12/2011 | Krulevitch et al. |
| 2012/0041363 | A1 | 2/2012 | ielDan |
| 2012/0043131 | A1 | 2/2012 | Christov et al. |
| 2013/0176020 | A1 | 7/2013 | Chauvin et al. |
| 2015/0367077 | A1 | 12/2015 | Plambech et al. |
| 2016/0008552 | A1 | 1/2016 | Madsen et al. |
| 2016/0015903 | A1 | 1/2016 | Madsen et al. |
| 2016/0175527 | A1* | 6/2016 | McCullough ........... A61M 5/00 604/111 |
| 2016/0287804 | A1 | 10/2016 | Madsen et al. |
| 2016/0287807 | A1 | 10/2016 | Madsen et al. |
| 2016/0287808 | A1 | 10/2016 | Madsen |

FOREIGN PATENT DOCUMENTS

| | | |
|---|---|---|
| EP | 1881859 B1 | 1/2011 |
| GB | 2456367 A | 7/2009 |
| WO | 96/19872 A1 | 6/1996 |
| WO | 9619872 A1 | 6/1996 |
| WO | 2005004955 A1 | 1/2005 |
| WO | 2006045525 A1 | 5/2006 |
| WO | 2008037801 A1 | 4/2008 |
| WO | 2008091838 A2 | 7/2008 |
| WO | 2008146282 A2 | 12/2008 |
| WO | 2009024562 A1 | 2/2009 |
| WO | 2010052275 A2 | 5/2010 |
| WO | 2010098927 A1 | 9/2010 |
| WO | 2010128493 A2 | 11/2010 |
| WO | 2011038703 A1 | 4/2011 |
| WO | 2011064299 A1 | 6/2011 |
| WO | 2012140097 A2 | 10/2012 |
| WO | 2013010889 A1 | 1/2013 |
| WO | 2013083715 A1 | 6/2013 |
| WO | 2013098421 A1 | 7/2013 |
| WO | 2014/128156 A1 | 8/2014 |
| WO | 2014/128157 A1 | 8/2014 |

* cited by examiner

ROTARY SENSOR MODULE WITH RESYNCHRONIZATION FEATURE

CROSS-REFERENCE TO RELATED APPLICATIONS

This application is a 35 U.S.C. §371 National Stage application of International Application PCT/EP2014/075180 (published as WO2015/075135), filed Nov. 20, 2014, which claims priority to European Patent Application 13193883.9, filed Nov. 21, 2013; this application claims priority under 35 U.S.C. §119 to U.S. Provisional Application 61/908,465; filed Nov. 25, 2013.

The present invention relates to devices, assemblies and systems adapted for capturing information in respect of rotational movement. In a specific aspect the invention addresses issues relating to electronic dose data capturing in and for a drug delivery device.

BACKGROUND OF THE INVENTION

In the disclosure of the present invention reference is mostly made to the treatment of diabetes by delivery of insulin using a drug delivery device, however, this is only an exemplary use of the present invention.

Drug delivery devices for injection have greatly improved the lives of patients who must self-administer drugs and biological agents. Drug injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems.

Correspondingly, a number of injection devices with a dose monitoring/acquisition feature has been provided, see e.g. in US 2009/0318865, WO 2010/052275 and U.S. Pat. No. 7,008,399. However, most devices of today are without it.

When a given device is provided with a position sensor it may occasionally need to be resynchronized or reset. For example, WO 2013/098421 discloses a pen device with two rotational and one axial sensor which are used for rotational resynchronization.

Having regard to the above, it is an object of the present invention to provide a drug delivery device as well as components and assemblies therefore which user-friendly, cost-effectively and reliably allows detection and storage of dose data related to use of a drug delivery device. It is a further object to provide such components and assemblies which could be used also in other applications having the same types of input.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a drug delivery device is provided comprising expelling means allowing a user to set a dose of drug to be expelled corresponding to a number of increments from an initial state. An indication member is adapted to rotate in a first direction corresponding to the set dose and rotate in an opposed second direction corresponding to a set dose being expelled, the indication member having an initial rotational position corresponding to both the initial state and a fully expelled dose state. The drug delivery device further comprises sensor means having an incremental counter synchronized with the rotational position of the indication member and having a reference point corresponding to the initial rotational position of the indication member. After detecting an error state the sensor means is adapted to re-synchronize by detecting the number of rotational increments for a set dose and for a subsequent expelled dose. If the numbers are identical the reference point is reset corresponding to the current rotational position of the indication member.

In the context of the present disclosure the term "indicator member" is used to identify the actual member for which rotation is detected, the detected rotation indicating the set and/or expelled dose of drug.

In a specific aspect of the invention a drug delivery device is provided comprising a housing, a drug-filled cartridge or means for receiving a drug-filled cartridge, the cartridge comprising an axially displaceable piston and a distal outlet portion, and drug expelling means. The drug expelling means comprises dose setting means allowing a user to set a dose of drug to be expelled, the dose corresponding to a number of increments from an initial state, an axially displaceable piston rod adapted to move the piston of a cartridge in a distal direction to thereby expel drug from a cartridge, an indication member adapted to rotate in a first direction relative to the housing and corresponding to the set dose, and rotate in an opposed second direction relative to the housing and corresponding to an expelled dose, the indication member having an initial rotational position corresponding to both the initial state and the fully expelled dose state, and actuation means for expelling a set dose, the drug expelling means being in an expelling state during expelling of a dose. The drug delivery device further comprises rotary sensor means having a synchronized state in which an incremental counter is synchronized with the rotational position of the indication member and has a reference point corresponding to the initial rotational position of the indication member, the sensor means being adapted to detect the number of rotational increments performed by the indication member in the first direction corresponding to a set dose, the number of rotational increments performed by the indication member in the second direction corresponding to an expelled dose, an expelling state for the expelling means, and a non-synchronized error state. When a non-synchronized error state is detected, the sensor means is adapted to automatically re-synchronize by (i) detecting the number of rotational increments for a set dose, (ii) in the expelling state, detecting the number of rotational increments for a subsequent expelled dose, and (iii) if the two numbers of increments are the same, reset the reference point corresponding to the current rotational position of the indication member.

Thus a drug delivery device is provided with a dose detecting system adapted to re-synchronize with the mechanical system based on information inherent in external standard operations performed on the system. In this way the device can be re-synchronized without involvement of the user.

The sensor means may be in the form of a sensor assembly comprising a first portion comprising a first rotary sensor part, the first rotary sensor part comprising a surface with a plurality of individual electrically conducting rotational position sensor segments arranged in a pattern, and a second portion comprising a second rotary sensor part arranged rotationally relative to the first portion, the second rotary sensor part comprising a plurality of rotational position contact structure adapted to be in contact with conducting rotational position sensor segments on the first sensor rotary part. In such an arrangement the rotational position contact structures are configured to engage and connect different rotational position sensor segments as the first and second rotary sensor part of the sensor assembly rotate relative to each, the created connections being indicative of a rotational position between the first and second sensor assembly portions. Sensor electronic circuitry is adapted to determine a rotational position between the first and second portions based on a given pattern of created connections.

The first rotary sensor part surface may further comprise an electrically conducting axial position sensor segment, and the second rotary sensor part may further comprise an axial position contact structure adapted to be in contact with the conducting axial position sensor segment on the first rotary sensor part. The axial position contact structure comprises an axial position contact having a connected position in which the axial position contact is in contact with the axial position sensor segment, and a dis-connected position in which the axial position contact is not in contact with an axial position sensor segment. In such an arrangement the connected position corresponds to the expelling state. The drug delivery device further comprises actuator means for axially moving the axial position contact between the connected and the dis-connected position.

The second rotary sensor part may be in the form of a metallic disc member comprising a plurality of integrally formed flexible arms forming the contact structures, at least one of the flexible arms being axially moveable to form a flexible switch arm comprising the axial position contact.

In an exemplary embodiment the sensor assembly is provided in combination with a housing, wherein the first portion is arranged rotationally relative to the housing, the second portion is arranged non-rotationally relative to the housing, and at least one of the first and second portions are arranged axially moveable relative to the housing. The actuator means is arranged between the housing and the second portion. The actuator means may be in the form of a mechanical connection formed between the housing and the flexible switch arm, whereby relative axial movement between the housing and the flexible switch arm moves the switch contact between the connected and dis-connected positions.

In a further exemplary embodiment a drug delivery device is provided comprising a sensor assembly as described above in combination with a housing, a drug-filled cartridge or means for receiving a drug-filled cartridge, the cartridge comprising an axially displaceable piston and a distal outlet portion, and drug expelling means. The drug expelling means comprises dose setting means allowing a user to set a dose of drug to be expelled, an axially displaceable piston rod adapted to move the piston of a cartridge in a distal direction to thereby expel drug from the cartridge, an indication member adapted to rotate corresponding to a set and/or expelled dose, and an axially moveable actuation member adapted to actuate the drug expelling means to thereby expel the set dose of drug. The first and second rotary sensor parts are arranged to rotate relative to each other during setting and expelling of a dose of drug, and the axial switch contact are arranged to be actuated between the two positions when the actuation member is moved axially.

The first rotary sensor part may be part of a sensor assembly first portion mounted to and rotating with the indication member, the first portion comprising electronic circuitry adapted to estimate an amount of expelled drug based on detection of rotational movement between the first and second rotary sensor parts corresponding to a set and an expelled dose. The indication member may be adapted to move axially between an initial and an actuated position, the first portion of the sensor assembly being mounted to move axially with the indication member. The second portion may be mounted to move axially with the indication member.

The electronic circuitry may be provided with logging means adapted to create a log for dose amounts of drug expelled from a cartridge by the drug expelling means, wherein the dose amounts are calculated based on relative rotation between the first and second rotary sensor parts during setting and/or expelling of a dose of drug. The first portion may be provided with a display which may be turned off during rotation of the first portion. The electronic circuitry may comprise transmitter means adapted to transmit stored data to an external receiver.

As used herein, the term "drug" is meant to encompass any flowable medicine formulation capable of being passed through a delivery means such as a cannula or hollow needle in a controlled manner, such as a liquid, solution, gel or fine suspension, and containing one or more drug agents. The drug may be a single drug compound or a premixed or co-formulated multiple drug compounds drug agent from a single reservoir. Representative drugs include pharmaceuticals such as peptides (e.g. insulins, insulin containing drugs, GLP-1 containing drugs as well as derivatives thereof), proteins, and hormones, biologically derived or active agents, hormonal and gene based agents, nutritional formulas and other substances in both solid (dispensed) or liquid form. In the description of the exemplary embodiments reference will be made to the use of insulin and GLP-1 containing drugs, this including analogues thereof as well as combinations with one or more other drugs.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. When it is defined that members are mounted axially free to each other it generally indicates that they can be moved relative to each other, typically between defined stop positions whereas when it is defined that members are mounted rotationally free to each other it generally indicates that they can be rotated relative to each other either freely or between defined stop positions. The terms "assembly" and "subassembly" do not imply that the described components necessary can be assembled to provide a unitary or functional assembly or subassembly during a given assembly procedure but is merely used to describe components grouped together as being functionally more closely related.

Figure 1:
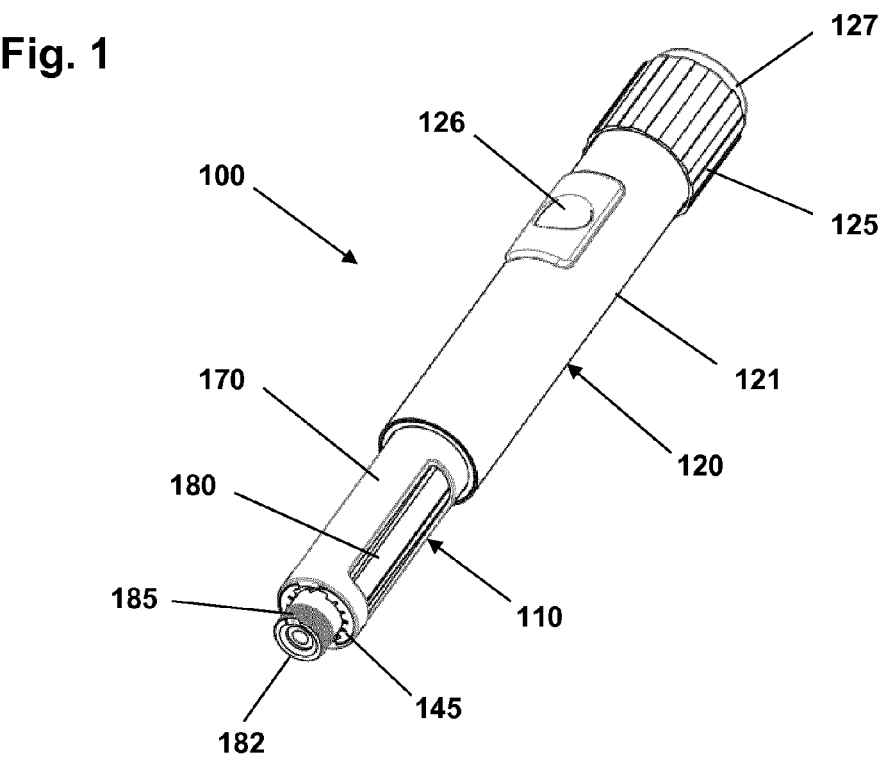
FIGS. 1 and 2 show a front-loaded drug delivery device with respectively without a drug cartridge mounted.

Referring to FIG. 1 a pen-formed drug delivery device 100 will be described. The device represents a "generic" drug delivery device providing an example of a device in combination with which embodiments of the present invention is intended to be used, such a device comprising an indicator member adapted to rotate corresponding to a set and/or expelled dose of drug.

More specifically, the pen device comprises a cap part (not shown) and a main part having a proximal body or drive assembly portion 120 with a housing 121 in which a drug expelling mechanism is arranged or integrated, and a distal cartridge holder portion in which a drug-filled transparent cartridge 180 with a distal needle-penetrable septum can be arranged and retained in place by a cartridge holder 110 attached to the proximal portion, the cartridge holder having openings allowing a portion of the cartridge to be inspected.

The cartridge may for example contain an insulin, GLP-1 or growth hormone formulation. The device is designed to be loaded by the user with a new cartridge through a distal receiving opening in the cartridge holder, the cartridge being provided with a piston driven by a piston rod 128 forming part of the expelling mechanism. A proximal-most rotatable dose ring member 125 serves to manually set a desired dose of drug shown in display window 126 and which can then be expelled when the release button 127 is actuated. Depending on the type of expelling mechanism embodied in the drug delivery device, the expelling mechanism may comprise a spring which is strained during dose setting and then released to drive the piston rod when the release button is actuated. Alternatively the expelling mechanism may be fully manual in which case the dose ring member and the release button moves proximally during dose setting corresponding to the set dose size, and then moved distally by the user to expel the set dose. The cartridge is provided with distal coupling means in the form of a needle hub mount 182 having, in the shown example, an external thread 185 adapted to engage an inner thread of a corresponding hub of a needle assembly. In alternative embodiments the thread may be combined with or replaced by other connection means, e.g. a bayonet coupling.

Figure 2:
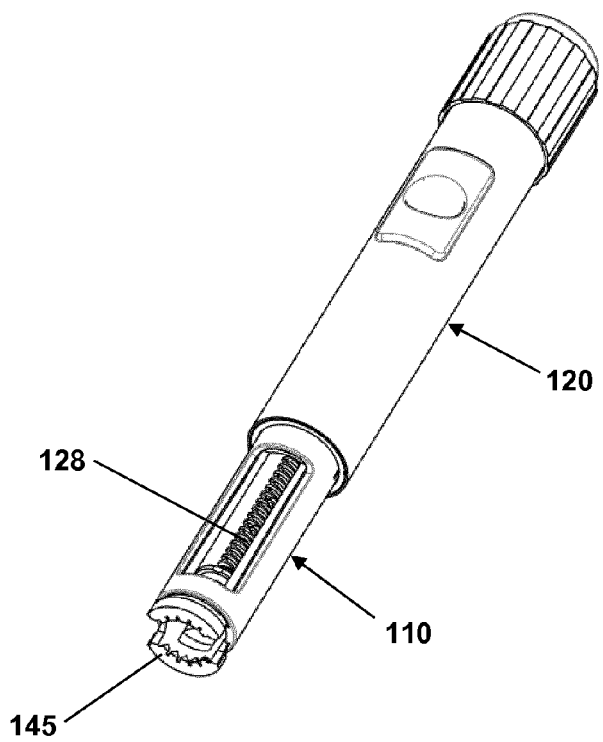

The cartridge holder comprises a distal opening adapted to receive a cartridge. More specifically, the cartridge holder comprises an outer rotatable tube member 170 operated by the user to control movement of gripping means to thereby open and close gripping shoulders 145 configured to grip and hold a cartridge. FIG. 2 shows the device with the cartridge removed and the gripping shoulders in their unlocked "open" position in which a cartridge can be removed and a new inserted.

As appears, FIG. 1 shows a drug delivery device of the front-loaded type in which a cartridge is inserted through a distal opening in the cartridge holder which in non-removable attached to the main part of the device, however, the drug delivery device may alternatively comprise a cartridge holder adapted to be removed from the device main portion and in which a cartridge is received and removed through the proximal opening.

Figure 3:
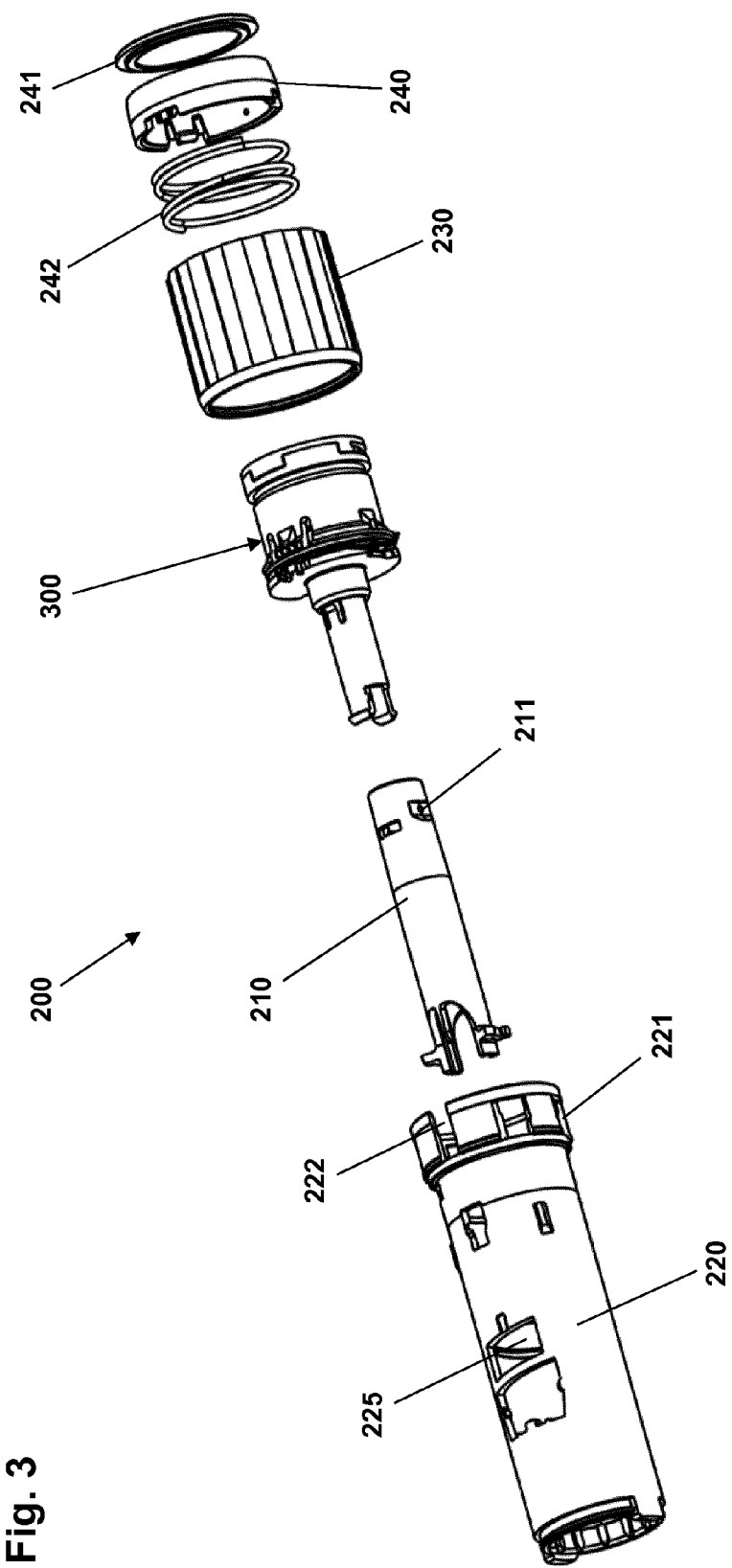
FIG. 3 shows in an exploded view a drug delivery device subassembly comprising a logging module.

With reference to FIG. 3 a subassembly 200 for a drug delivery device will be described, the subassembly comprising a logging module in combination with parts of the drug delivery device being directly functionally related to the incorporation and operation of logging unit. More specifically, the subassembly comprises an electronically controlled logging module 300, an inner tube member 210, a generally cylindrical inner housing member 220, a dial ring member 230 and a button assembly comprising a button ring 240, a button window 241 and a button spring 242. The inner housing member is configured to be arranged inside an outer housing member providing the exterior of the drug delivery device.

Figure 4:
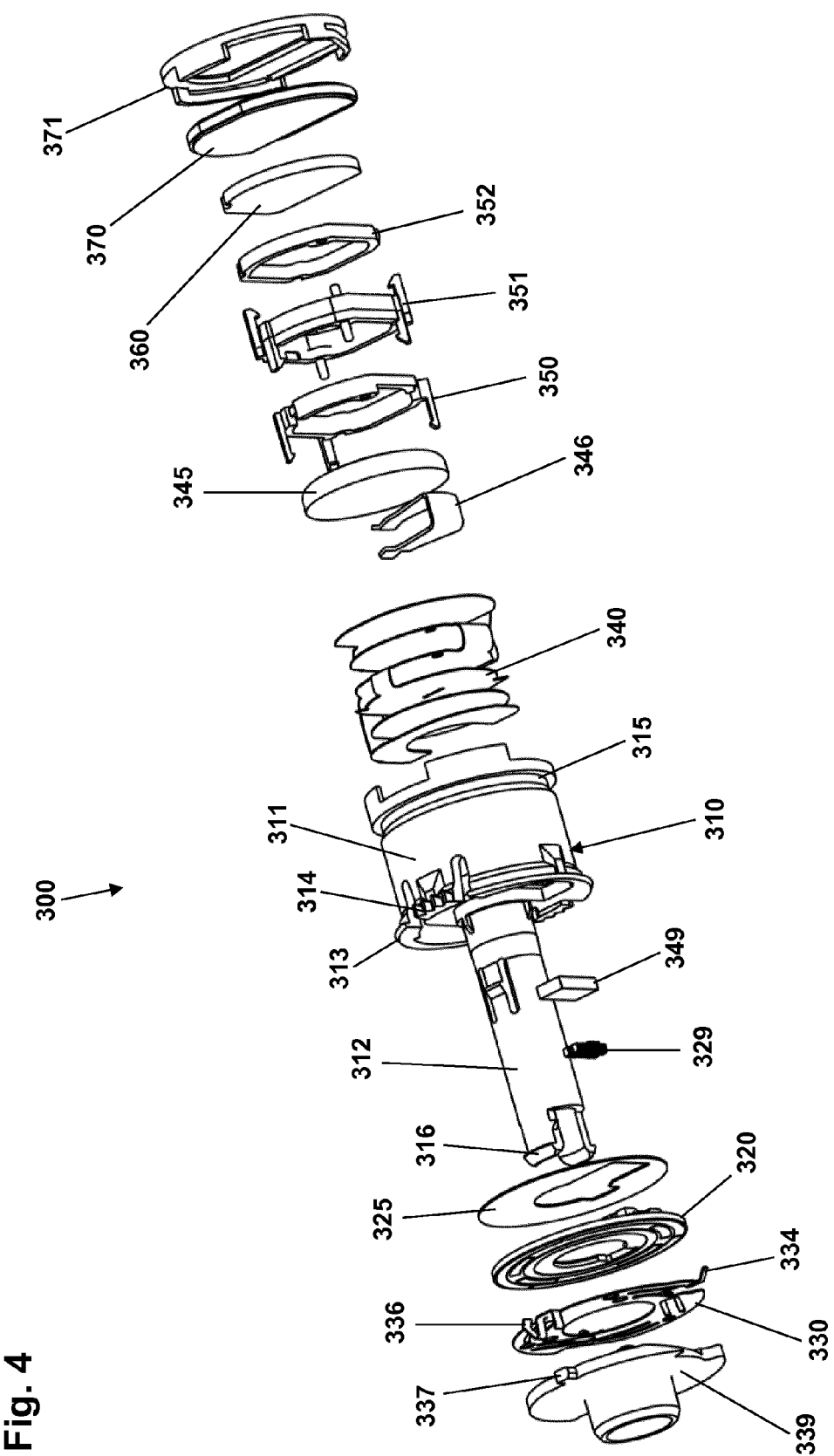
FIG. 4 shows an exploded view of the logging module of FIG. 3, FIGS. 5 and 6 show first respectively second rotary sensor parts of the module of FIG. 3.

The different components of the logging module 300 are shown in FIG. 4. More specifically, the logging module comprises a housing member 310 having a barrel-shaped proximal main portion 311 with a distally extending tube portion 312, a mounting foil member 313, a disc-formed first rotary sensor part 320 onto which a first connector 329 is to be mounted, a disc-formed second rotary sensor part 330, a rotary sensor holder 339 with a lateral projection 337, a flexible PCB 340 folded in a multi-layered stack and onto which a second connector 349 is to be mounted, a battery 345 and battery clip 346, a number of mounting rings 350, 351, 352, an antenna 360, an LCD 370 and an LCD frame 371. On the PCB electronic circuitry components are mounted, e.g. micro-controller, display driver, memory and wireless communication means. As will be described below in greater detail the first rotary sensor part 320 comprises a plurality of arc-formed discreet contact areas, and the second rotary sensor part 330 comprises a plurality of flexible contact arms of which the outer ones provide flexible switch arms 333 having a laterally extending switch projection 334.

Figure 5:
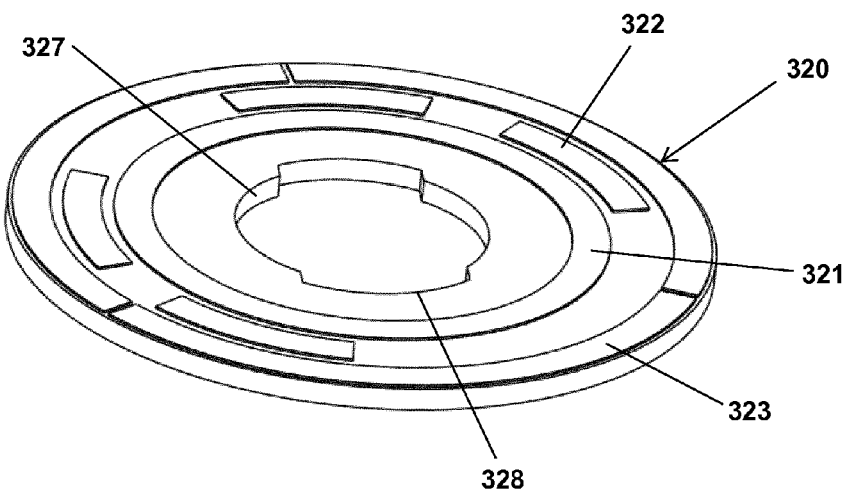

FIG. 5 shows the first rotary sensor part 320 comprising a ring-formed disc formed from circuit board material and on which a number of contact areas (or segments) has been plated on forming three concentric rings, an inner, an intermediate and an outer ring. The disc comprises a central opening 327 with two opposed cut-outs 328 allowing the disc to be mounted non-rotationally on e.g. tube portion 312. In shown embodiment the inner ring is a single contact area 321 used as ground (i.e. reference), the intermediate ring comprises four discrete arch-formed rotational position sensor segments 322 arranged with a certain circumferential distance there between, and the outer ring comprises three discrete arch-formed axial position sensor segments 323 arranged with only a small circumferential gap there between, the segments being individually connected to a given contact terminal of the multi-terminal connector 329 mounted on the rear (proximal) face of the disc. If a given segment is not connected to a terminal it can be considered a passive segment.

Figure 6:
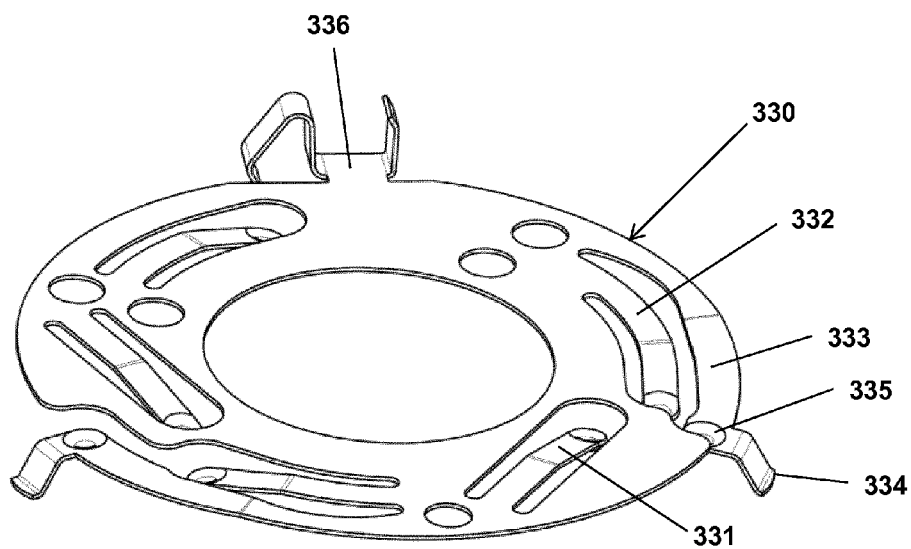

The second rotary sensor part 330 shown in FIG. 6 is in the form of a metallic disc comprising a number of flexible arc-formed contact arms protruding proximally, the distal end of each contact arm 331, 332, 333 comprising a dome-formed contact 335 with a contact point (facing downwards in the figure) adapted to create a galvanic connection with a given contact area. The contact arms are arranged corresponding to the three concentric rings of the first rotary sensor part. More specifically, the second rotary sensor part comprises two inner contact arms 331, three intermediate contact arms 332 and two outer contact arms 333.

In this way a given pair of contact arms provides a combined contact structure adapted to create electric contact between two sensor segments. In the shown embodiment the two inner ground contact arms 331 are provided to be in contact with the single ground contact area 321 of the inner concentric ring, the three rotational position contacts arms 332 are provided to be in contact with the four rotational position sensor segments 322 of the intermediate concentric ring, and the two outer axial position contact arms 333 are provided to be in contact with the three axial position sensor segments 323 of the outer concentric ring, the outer axial position contact arms carrying the laterally extending switch projection 334. Indeed, for the intermediate and outer contact arms the rotational position between the two sensor parts will determine which sensor segment is engaged with a given contact arm.

In the shown embodiment the gaps between two neighbouring outer sensor segments are dimensioned such that the dome-formed contact point will be in contact with both segments as it moves from one segment to the next, this being explained in greater detail below. The second rotary sensor part further comprises a gripping part 336 adapted to engage the projection 337 on the rotary sensor holder 339 to prevent rotational movement there between.

In the shown embodiment the intermediate arms and intermediate sensor segments provide a rotational position sensor system whereas the outer arms and outer sensor segments provide an axial position sensor system as will be described in greater detail below.

Figure 7:
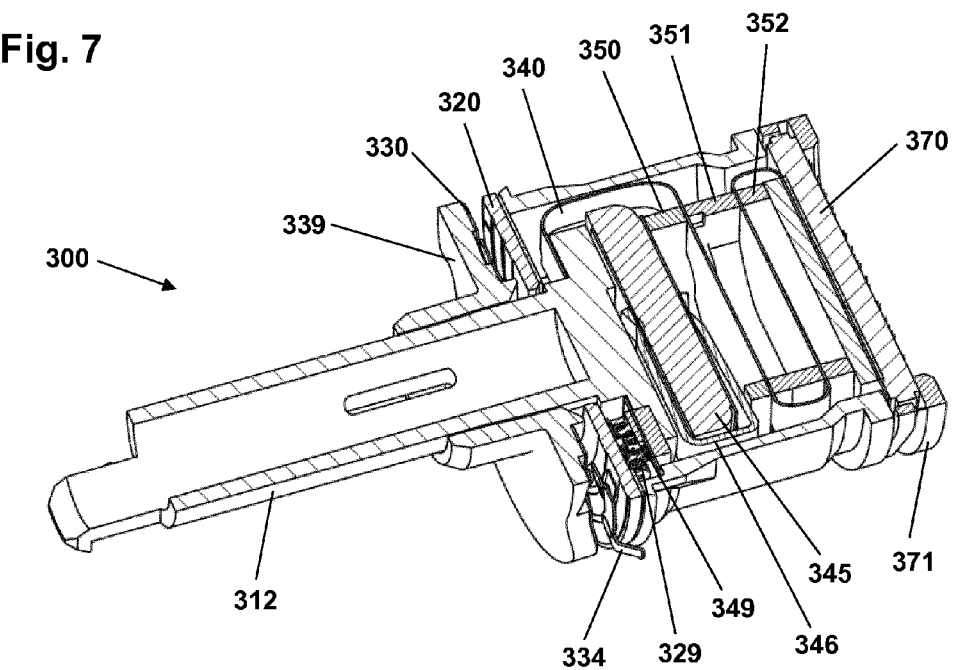
FIG. 7 shows the logging module of FIG. 4 in an assembled state.

FIG. 7 shows the logging module 300 in an assembled state. The flexible PCB 340 with its mounted components and the antenna have been mounted in a sandwich configuration with the mounting rings 350, 351, 352 providing the required spacing and attachment via e.g. gluing or adhesives, the battery 345 being attached to the PCB via battery clip 346. The PCB sandwich is mounted with a "tongue" threaded through a distal opening in the housing 311 button portion and held in place with adhesive mounting foil member 325 (see FIG. 4) during assembly. The first rotary sensor part 320 is mounted non-rotationally on the tube portion 312 and connected to the PCB via the connectors 329, 349. The second rotary sensor part 330 is mounted non-rotationally and axially fixed on the rotary sensor holder 339 which is mounted rotationally free but axially fixed on the tube portion 312. By this arrangement the flexible rotary sensor arms are held in sliding contact with the contact surfaces. The LCD 370 is mounted on top of the PCB sandwich which together is held in place in the housing barrel by the display frame 371 which is permanently attached to the housing by e.g. welding. As appears, in this way an electronic logging module is provided comprising a distally arranged rotatable sensor part. As shown in FIG. 4 the housing main portion 311 comprises a circumferential distal flange 313 with a number of proximally projecting teeth 314 and a circumferential proximal groove 315. The tube portion 312 is provided with distal snap connectors 316 adapted to engage corresponding openings 211 in the inner tube member 210.

Figure 8:
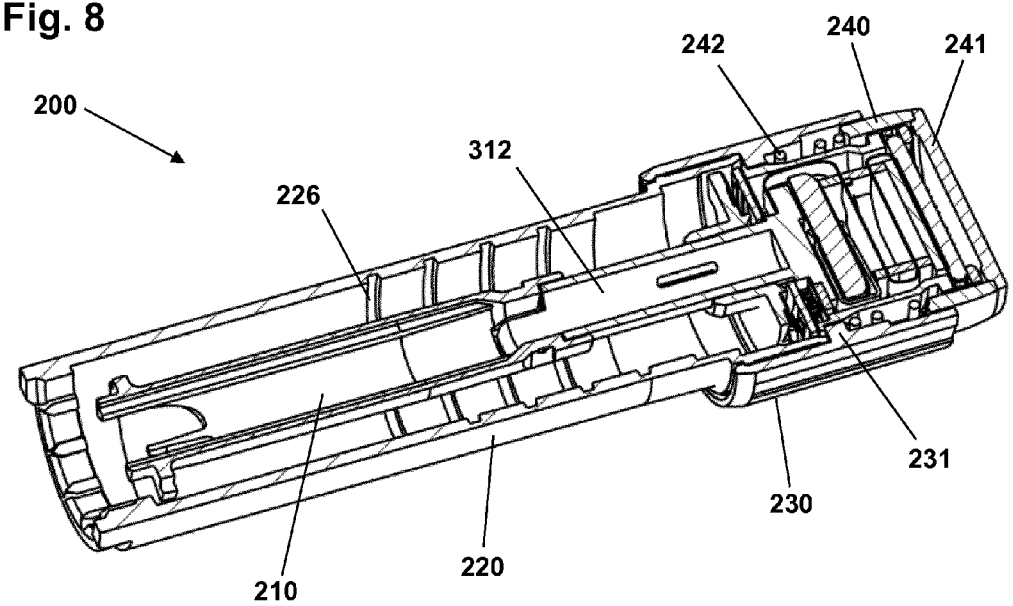
FIG. 8 shows a cross-sectional view of the subassembly of FIG. 3 in an assembled state.

FIG. 8 shows a cross-sectional view of the subassembly 200 in an assembled state. The term "subassembly" does not imply that the shown parts necessary are assembled to provide a subassembly as shown and which can be used in an assembly process for a given drug delivery device. In contrast, the shown logging module of FIG. 7 may be provided in the shown form as a "real" subassembly. Referring to the parts shown in FIGS. 3 and 4, the inner tube member 210 is connected rotationally and axially locked to the distal tube portion 312 of the logging module. This arrangement is mainly for the purpose of moulding and subsequent assembly. The dial ring member 230 is mounted on the proximal portion of the housing member 220 on which it is allowed to freely rotate but not move axially. The dial ring member 230 comprises an inner circumferential coupling flange 231 with a plurality of distally facing teeth adapted to engage the proximally facing teeth 314 of the logging module to thereby rotationally lock the two components during engagement. The housing member 220 comprises first and second openings or cut-outs 221, 222 adapted to engage respectively the rotary sensor holder lateral projection 336 and the switch projection 334, this ensuring non-rotational engagement between the second rotary sensor part and the housing yet allows axial movement.

The button 240 with the window 241 attached is mounted on the module housing in gripping engagement with the circumferential groove 315, this allowing the button to rotate relative to the module housing. The axially compressed button assembly spring 242 is arranged in the circumferential gap between the module housing and the dial ring member and held in place between a distally facing ring portion of the button ring and the proximally facing portion of the coupling flange. In this way the spring provides an axial force biasing the module proximally into non-rotational engagement with the dial ring member 230 via the coupling flange, however, when a distally directed force is applied to the module via the button the module can be moved distally and thereby out of the rotational coupling with the dial ring member, this allowing the logging module main housing to rotate relative to the dial ring member.

Figure 9A:
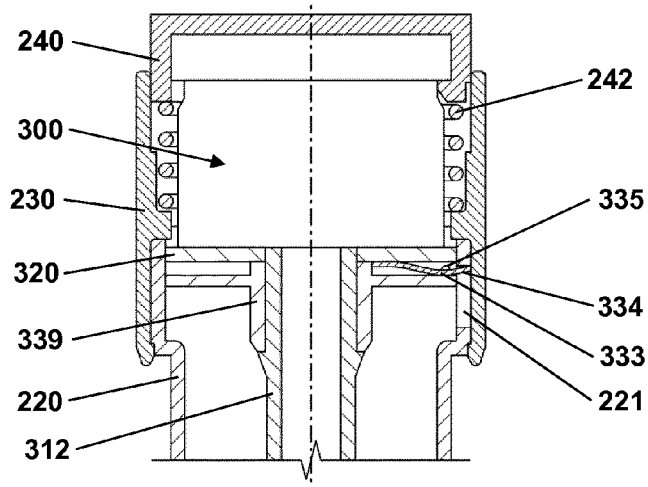
FIGS. 9A-9C show operation of an axial switch of the logging module in different operational states.
Figure 9B:
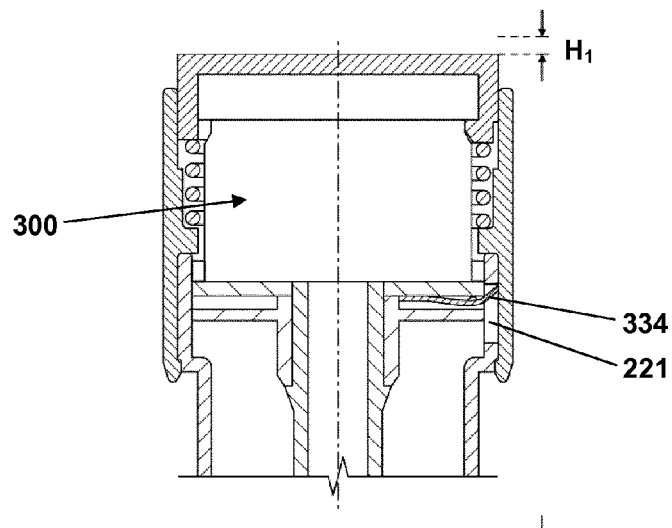
Figure 9C:
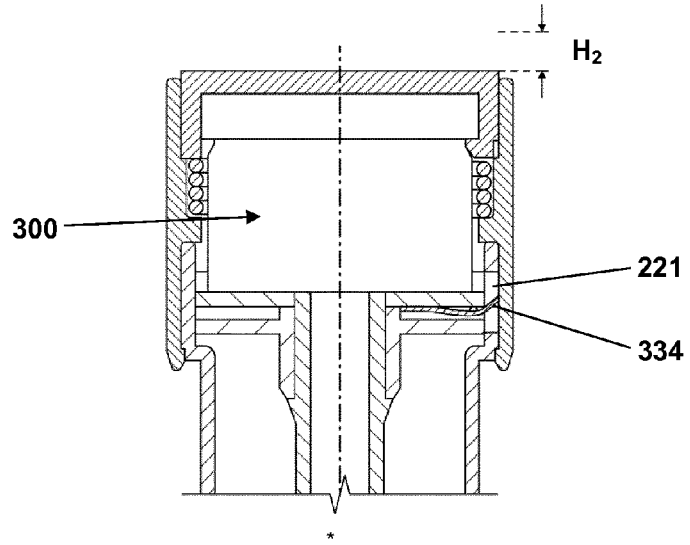

As indicated above, the shown rotary sensor comprises an axial position sensor system serving to detect an axial position of the logging module relative to (here) the housing member 220. More specifically, FIG. 9A shows the logging module 300 biased into an initial proximal position by the button spring 242, FIG. 9B shows the logging module in an intermediate position in which it has been moved distally by the distance $H_1$, and FIG. 9C shows the logging module in an actuated distal position in which it has been moved distally by the distance $H_2$. In all three states the switch projection 334 is positioned in the corresponding housing opening 221 and rotationally locked to the housing via the rotary sensor holder 339. As appears, in FIG. 9A the switch projection 334 engages a proximal edge of the opening and the flexible switch arm 333 with the contact point 335 is thereby held out of contact with the first rotary sensor part 320, in FIG. 9B the switch projection 334 still engages the proximal edge of the opening, however, the logging module has been moved distally and thereby the first rotary sensor part 320 has been moved into contact with the switch arm 333, this bringing the axial switch into an "on" state detectable by the logging module circuitry, and in FIG. 9C the logging module has been moved further distally to its actuated distal position. The switch projection 334 has been moved out of engagement with the proximal edge of the opening, the axial position sensor system thus remaining in its "on" state. In an exemplary embodiment the axial movement between the different positions may be e.g. 1.5 mm, this ensuring that the expelling mode is safely registered by the axial position sensor system before the dosing mechanism is actually released. The axial position sensor system could also be used to control the functioning of the logging module when no dose has been set, see below.

Figure 10:
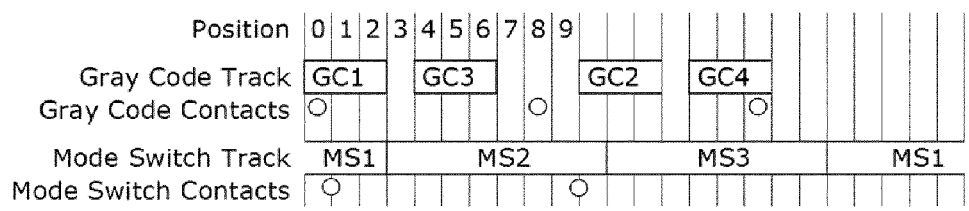
FIG. 10 shows a schematic representation of how tracks and contacts of a rotary sensor can be arranged.

Returning to the first and second rotary sensor parts of FIGS. 5 and 6 the intermediate arms and sensor segments provide the rotational position sensor system whereas the outer arms and sensor segments provide an axial position sensor system as will be described in greater detail below. This is illustrated in FIG. 10 in which the intermediate sensor segments provide a "Gray Code Track" with the sensor segments denoted "GC", the intermediate arms provide "Gray Code Contacts", the outer sensor segments provide a "Mode Switch Track" with segments denoted "MS" and the outer arms provide "Mode Switch Contacts". As also illustrated in FIG. 10 the described rotary sensor has a resolution of 15 degrees, i.e. 24 steps for a full rotation with only steps 1-9 numbered in the figure, such that for each 15 degrees of rotation a pre-determined change in which of the individual rotational position sensor segments are on and off is created. As each of the shown sensor segments is connected to the electronic circuitry 340 it is possible to determine the relative rotational position between the two rotary sensor parts (see below).

In respect of the above-described axial position sensor system, if using only one switch arm there would be a single point of failure when the information is to be detected by electrical means. Correspondingly, as shown in FIG. 6, two axial position switch arm are provided, however, providing redundancy by merely adding a further contact would introduce a new single point of failure should one of the contacts fail. Accordingly, the axial position sensor system of the described embodiment has been designed to allow detection of failure of one of the two axial position switches, this allowing the system to take appropriate action, e.g. indicating an error condition, before the system will actually malfunction.

More specifically, as shown in FIG. 5 the conductive outer ring has been split up in 3 sensor segments 323 identified as MS1, MS2 and MS3 in FIG. 10. When the flexible outer switch arms 333 are moved into contact with the conductive ring, the arms and segments are arranged such that conductive contact will be established with at least two of the three segments. During a full rotation the arms will move over the three sensor segments when the arms are pressed down, and thus give the following code pattern (24 steps for a full rotation), where the value "0" means that an arm is in contact with a segment:

| MS1 | MS2 | MS3 |
| --- | --- | --- |
| 0 | 0 | 1 |
| 0 | 1 | 0 |
| 1 | 0 | 0 |
| 1 | 0 | 0 |
| 1 | 0 | 0 |
| 1 | 0 | 0 |
| 1 | 0 | 0 |
| 1 | 0 | 0 |
| 0 | 0 | 1 |
| 0 | 1 | 0 |
| 0 | 1 | 0 |
| 0 | 1 | 0 |
| 0 | 1 | 0 |
| 0 | 1 | 0 |
| 0 | 1 | 0 |
| 1 | 0 | 0 |
| 0 | 0 | 1 |
| 0 | 0 | 1 |
| 0 | 0 | 1 |
| 0 | 0 | 1 |
| 0 | 0 | 1 |
| 0 | 0 | 1 |

In case the arms are not pressed down, the values for the three segments are 1,1,1.

If one of the axial position sensor segments or contact arms is faulty, the code pattern will be different from the above pattern. For example, if MS1 is faulty with the value "1" when the arms are pressed down then the first code would be 1,0,1. This fault is detectable since only one of the sensor segments has the value "0" (at least two "0" is expected in a healthy system), this allowing a single contact failure to be detected. Theoretically, if one functioning contact arm was bridging the gap between two neighbouring sensor segments and the other contact arm was faulty, then this would represent a non-error condition with two "0" values. However, if error detection is performed during rotation this special condition could be detected and disregarded. If MS1 is faulty with the value "0" when the arms are not pressed down then this fault is detectable since the values for the three segments should be 1,1,1 when the arms are not pressed down.

Although not implemented in the described embodiment, the outer contacts could also be used to provide additional rotational position information to the system.

Figure 11A:
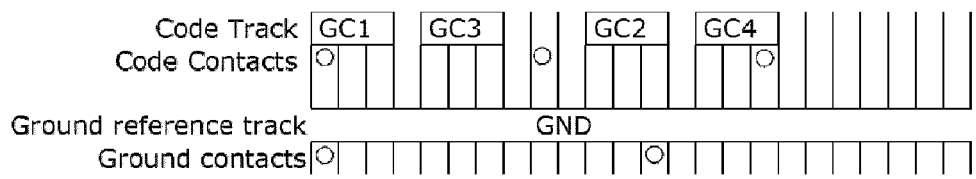
FIG. 11A shows a further schematic representation of how tracks and contacts of a rotary sensor can be arranged.

Returning to the first and second rotary sensor parts of FIGS. 5 and 6 the intermediate arms and sensor segments provide the rotational position sensor system whereas the inner arms and single circumferential segment provide a ground contact. This is illustrated in FIG. 11A in which the intermediate segments provide a "Code Track" with the segments denoted "GC" and the intermediate arms provide "Code Contacts" as in FIG. 10. The inner segment provides a "Ground reference track" denoted "GND" and the inner arms provide "Ground contacts".

Figure 11B:
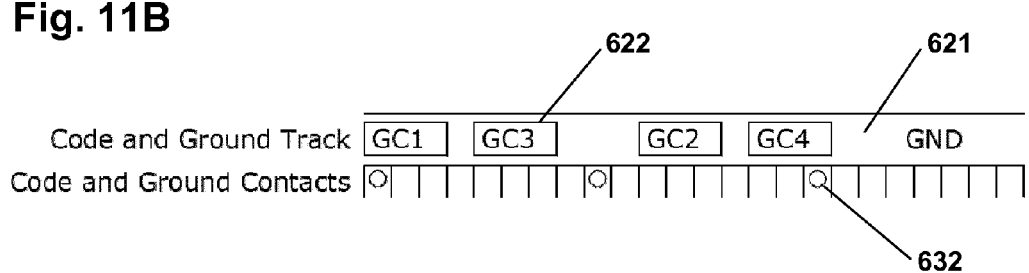
FIG. 11B shows a schematic representation of an alternative arrangement of tracks and contacts for a rotary sensor.

In an alternative embodiment shown schematically in FIG. 11B the code track and the ground reference track GND has been combined to a single "Code and Ground Track" by "superimposing" the code segments 622 onto the ground track 621 just as the dedicated ground contacts have been removed, the former code contacts now serving as combined code and ground contacts 632. More specifically, the code segments have been arranged as isolated "islands" in the ground track, this providing a single combined code and ground track in which a given circumferential portion is represented by either a code segment or a ground segment, whereby a given combined code and ground contact will be in contact with either a code segment or one of the ground segments. As shown in FIG. 11B the ground segments are connected to electrically form a single combined ground segment. In the shown embodiment the individual ground segments are connected by narrow strips of plating surrounding the radial sides of the code segments, this giving the code segments an "island" appearance, however, the ground segments could be connected e.g. on only one side of the code segments or via connections formed on the opposed side of the disc.

In the shown embodiment the code segments, the ground segments and the individual combined code and ground contact arms are arranged such that for a given rotational position at least one of the arms will be in contact with a ground segment, the remaining arms being in contact with a code segment to provide positional information. As appears, by this arrangement it is possible to maintain the same functionality as with two separate tracks and dedicated arms for each track.

In systems of the above type in which movement of mechanical components is detected by an electronic system that detects specific characteristics of the movements of the mechanical parts it is important that the electronic sensor system is correctly synchronized with the mechanical system. A traditional way to secure that the two systems are synchronized is to provide an absolute reference point on which determination is based. For example, WO 2012/140097 discloses a drug delivery device with a dose sensing system in which an end-of-dose contact is provided this providing that the two systems are synchronized at the end of any out-dosing event.

If no such system-provided synchronization takes place regularly and the electronic sensor system for some reason get outs of synchronization with the mechanical system, meaning that the mechanical parts have moved more or less than the electronic sensor system has detected, there is a need for the electronic sensor system to (i) know that it is out of synchronization, and to (ii) know when it is synchronized again with the mechanical system, in order to provide reliable information regarding the amount of movement detected. Detection of an out-of-synchronization condition could be performed electronically by e.g. analysing the stream of sensed code positions and identify an "illegal" code or sequence indicative of an error condition.

In the following an example of error detection for a system having the following specifications will be given:
A mechanical system bi-directionally operational between a mechanical minimum position and a mechanical maximum position in a number of pre-determined steps, e.g. between 0 and 100 dose units for an insulin delivery device.

An electronic sensor system adapted to detect each incremental mechanical step, and have a relative, repeating positioning of 0 to 7, i.e. the mechanical positions 0, 8, 16 and so forth give the electronic sensor positions of 0, mechanical positions 1, 9, 17 and so forth gives the electronic sensor positions of 1, etc.

One or more counters that increment up and down from e.g. 0 to 100, depending on the change in position in the electronic sensor positions and other inputs. An increment of 1 in the electronic sensor position results in an increment of a counter of 1.

For such a system rules 1 to 5 are implemented and checked each time a sensor change occurs. Every time at least one of the rules is met, the counter(s) are reset (e.g. set to 0), and the system is determined to be out of synchronization.

1. Sensor code invalid (sensor information does not contain position indication)
2. Sensor code sequence invalid (e.g. jumping directly from electronic sensor position 2 to 5 in one sensor value change)
3. Counter<Minimum mechanical position
4. Counter>Maximum mechanical position
5. Sensor code not correlated to Counter (e.g. sensor code is related to position 3 in the electronic sensor system, but the counter value is 5)

If delivery of a dose of drug is performed during which a synchronization error is detected the system will not record a dose log entry for that event and may indicate to the user after delivery that a detection error occurred.

To help the system re-synchronize the user of the system could be asked to help the electronic system get back into synchronization by performing specific actions onto the system. As an alternative, the above-described drug delivery device may be provided with a dose detecting system adapted to re-synchronize with the mechanical system based on information inherent in external standard operations performed on the system, i.e. without involvement of the user.

More specifically, this feature is based on the fact, that the user will execute standard actions on the system, which the electronic sensor system is designed to detect. In this case detection of amount of movement of mechanical parts which at the start and the end of the execution of a standard action, are positioned at an absolute reference point. First time the user executes a standard action on the system, after the system has lost synchronization, and the resulting mechanical movements has been detected correctly by the electronic sensor system, the electronic system at the end of standard action is determined by itself to be in synchronization with the mechanical system.

For example, the sensor means may be adapted to automatically re-synchronize by (i) detecting the number of rotational increments for a set dose, (ii) in the expelling state, detecting the number of rotational increments for a subsequent expelled dose, and (iii) if the two numbers of increments are the same, reset the reference point corresponding to the current rotational position of the indicator member.

Although the described resynchronisation process is based on an assumption that detected values represent certain specific actions, it is considered that the described concept in a user-friendly way provides re-synchronization with a high reliability.

The parts of the subassembly 200, apart from module 300, as shown in FIG. 3 represent "generic" parts of a drug expelling mechanism having properties which are relevant for the implementation of embodiments of the present invention. More specifically, the shown module 300 is adapted to be implemented in a drug delivery device having a housing, dose setting means allowing a user to set a dose of drug to be expelled, and an indicator member adapted to rotate corresponding to a set and/or expelled dose. In the shown subassembly the inner tube member 210 represents a "generic" indicator member.

Although not part of the present invention, in the following a short description of a drug expelling mechanism into which the shown inner tube member 210 could be integrated will be described. When setting a dose to be expelled the user rotates the dial ring member 230 and thereby the inner tube member 210 to a given rotational position representing a desired dose, this straining a torsional spring member arranged around the tube member and attached at its proximal end to a housing proximal portion and at its distal end to the tube member distal portion. A ratchet coupling arranged at the distal end of the inner tube member serves to hold the now rotationally biased tube member in the set position. A scale drum is coupled to and rotates with the tube member, the scale drum having a threaded connection with the housing (e.g. threads 226 in FIG. 3) whereby a spirally arranged series of numeric values is moved relative to a window in the housing (e.g. opening 225 in FIG. 3), the shown number indicating the presently set dose. To release the set and loaded mechanism the user pushes a proximal release button whereby the inner tube member is moved distally. By this action the ratchet coupling (serving as a release member) is released and the inner tube member is moved into engagement, directly or indirectly, with a rotational drive member, the drive member being arranged to rotate a piston rod which due to a threaded engagement with the housing is moved distally to thereby the set dose. As the tube member rotates backwards, thereby driving the piston rod distally, also the scale drum is rotated backwards and reaches its initial "zero" position together with the tube member. This kind of mechanism is known from e.g. the FlexTouch® drug delivery pen device marketed by Novo Nordisk for the injection of e.g. insulin formulations.

As appears, in the described exemplary mechanism the inner tube member 210 (to which the main portion of the logging module 300 is rigidly mounted) rotates relative to the housing 220 during both setting and expelling of a given dose. As the second rotary sensor part 330 is rotationally locked to the housing, also the two rotary sensor parts 320, 330 rotate relative to each other during both setting and expelling of a given dose. As this is merely an exemplary mechanism, other mechanisms can be envisaged in which a given member rotates only during setting or expelling.

This said, in the shown embodiment the logging module is adapted to detect rotation in both directions corresponding to a set dose and an expelled dose. In the shown embodiment the logging module is further provided with an axial switch allowing the module to detect whether the mechanism is in the setting or expelling mode, however, this is an optional feature. In the shown embodiment the code pattern has a step "resolution" of 15 degrees of rotations which for a given drug formulation and delivery device combination may correspond to 1 unit (IU) of insulin. Indeed, for a drug formulation having the double concentration a 7.5 degree rotary resolution would be necessary to register dose steps corresponding to 1 IU of insulin. The rotary sensor comprising the rotary contacts and the associated electronic circuitry could be designed to detect the amount of rotation using a number of designs, e.g. each 15 degrees increment may be counted, or a given position may be detected absolutely within sectors of e.g. 120 or 360 degrees, a counter registering the number of completed sectors. Such a counter could be implemented using the switch arms and outer contact areas described with reference to FIGS. 5 and 6. With a "counting" design it is important that the first increment is registered, however, modern electronics can be operated in a low-power "on" state avoiding the delay normally associated with a wake-up change of state from a "sleep" state to an "on" state.

In an exemplary embodiment the rotary sensor is designed to count the number of steps during setting and to count down the number of steps during expelling, with the expelling steps being registered in the log as the dose being expelled. By counting in both directions proper registering and functioning of the logging module can be assured to a high degree. As a given dose of drug, especially if large, may be divided and injected with a given pause, the logging module may be programmed to log two dose amounts expelled within a given time window, e.g. 15 minutes, as one dose.

The logging module may be configured to store and show data in different ways. To many users the time since last dose and the size of that dose are the most important values. To other users and/or a medical practitioner an overview of the entire log for a given period, e.g. a week or a month, may be of importance. To allow such an overview the logging module may be provided with output means allowing the dose log to be transferred, e.g. by NFC transfer, to an external display device, e.g. a smartphone or computer for better graphic overview, see below.

To ensure that the full dose is expelled the logging module may be set up to display the last expelled dose only when the expelling mechanism has been returned to zero. Otherwise a given "half" dose will be stored in the log but not displayed. For example, if a dose of 40 IU is dialled and 20 IU are expelled immediately thereafter the display will not show data for that delivery. To have the dose shown in the display the user may expel the remaining dose and the combined dose of 40 IU together with a time stamp will be shown in the display. Alternatively the user may dial the expelling mechanism back to zero and the display will show 20 IU, or the user may dial the expelling mechanism back to 10 IU and expel the 10 IU and the display will show 30 IU. Indeed, for the expelled amounts to be combined the two (or more) doses will have to be expelled within the above-described time window, e.g. 15 minutes. Otherwise only the last portion of the dose will display, the first portion being stored merely as an entry in the log.

The display can be configured to show data in different formats. For example, the display 411 of FIG. 10 is a two-line display in which time is shown using a HH:MM:SS stop watch design, this providing that the time since the last dose expelled from the device can be shown with a running second counter allowing a user to easily identify the shown information as a counting time value. After 24 hours the display may continue to display time in the HH:MM:SS format or change to a day and hour format.

To save energy the display will turn off after a pre-determined amount of time, e.g. 30 seconds. To turn on the display again the user may e.g. press the button thereby using the axial switch to turn on the display, or the display may be turned on when the dose dial is turned away from and then back to zero.

A user may desire to check the dose log directly on the module display. Toggling through the dose log could also be controlled by the axial switch, e.g. two fast pushes on the button 412 will bring the module into log display mode, each consecutive push on the button recalling the next log entry. The module may leave the log display mode automatically after a given amount of time, or the user may bring the module into normal display mode by e.g. dialling back and forth as described above. As an alternative, the electronic module may be provided with other types of input means, e.g. a motion sensor which would allow a user to turn on the display by shaking or tapping, or a touch sensor integrated in the display as is well known from e.g. smartphones which would allow a user to turn on the display by swiping a finger across the display.

Figure 12:
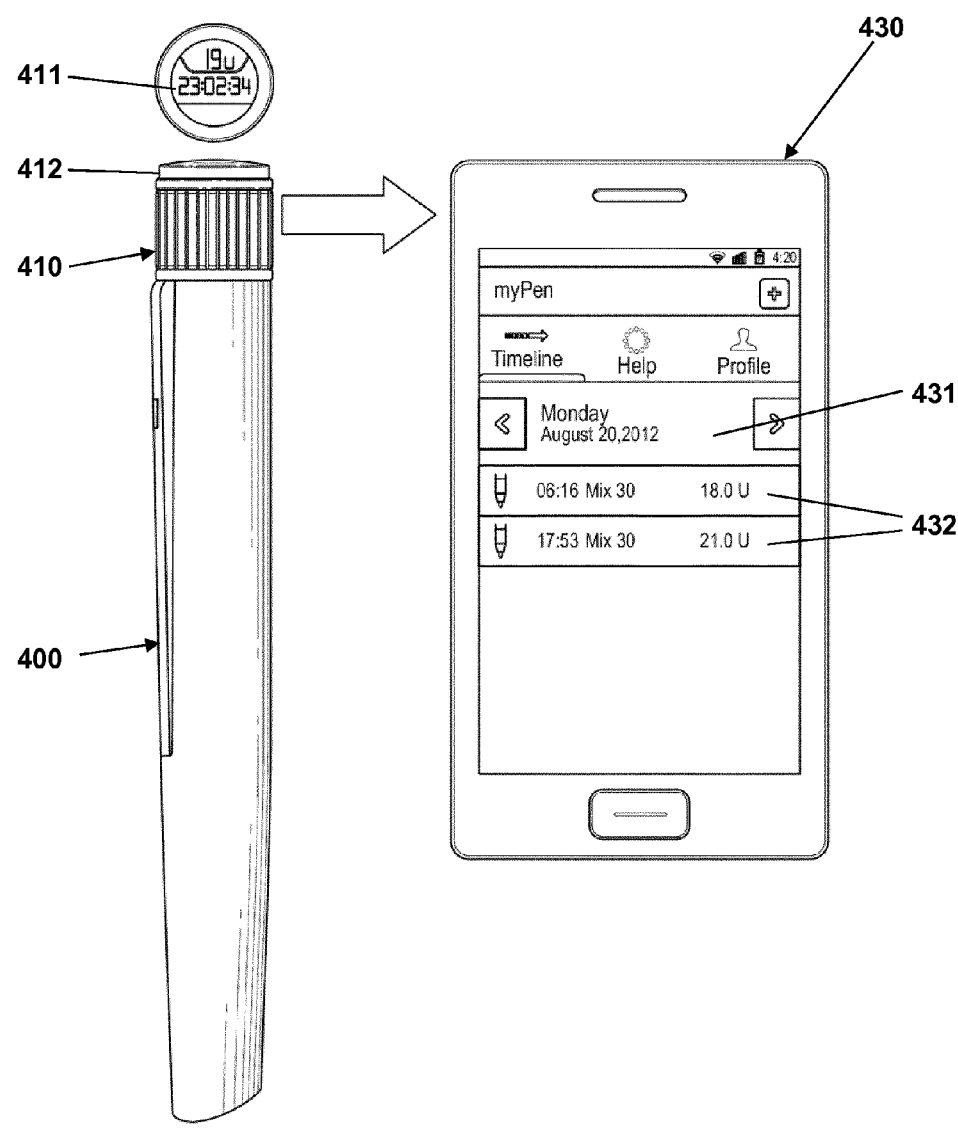
FIG. 12 shows a drug delivery pen provided with a logging module and in communication with a smartphone.

FIG. 12 shows a drug delivery pen 400 provided with a logging module 410 as described above and arranged next to a smartphone 430 configured to receive logging data from the logging module via wireless communication, e.g. NFC or Bluetooth®. As appears, the logging module is provided with a display configured to indicate the size of the last dose and the time since the last dose using the stopwatch display mode.

In order to communicate with the logging module the smartphone has been provided with specific "insulin diary" software. When the software is activated to initiate data transfer the smartphone NFC transmitter will transmit specific code which will wake up any nearby logging module which will then retransmit a unique code identifying the specific module. If a specific code is received for the first time the user is asked to confirm pairing and is asked to select from a list the given drug that should be associated with the given logging module, e.g. "Mix 30" as shown. In this way the smartphone can create an insulin diary covering more than one drug. In the described simple "manual" set-up the user has to ensure that a correct cartridge, e.g. with Mix 30 insulin, is loaded in a drug delivery pen which has been associated with that type of drug. Indeed, other set-ups can be envisaged, e.g. a given pen may be (mechanically) coded to only accept a given type of cartridge with the designated type of drug, or the pen and logging module may be provided with the ability to identify different types of cartridges and thus types of drug.

In the shown embodiment log data from a logging module associated with a Mix 30 insulin has been transferred. In the exemplary user interface the user can toggle back and forth between different day views, each day view showing the different amounts of drug delivered together with a real time value. In FIG. 12 on a given day 431 first and second amounts 432 of Mix 30 has been delivered with the time and amount shown for each delivery.

Figure 13:
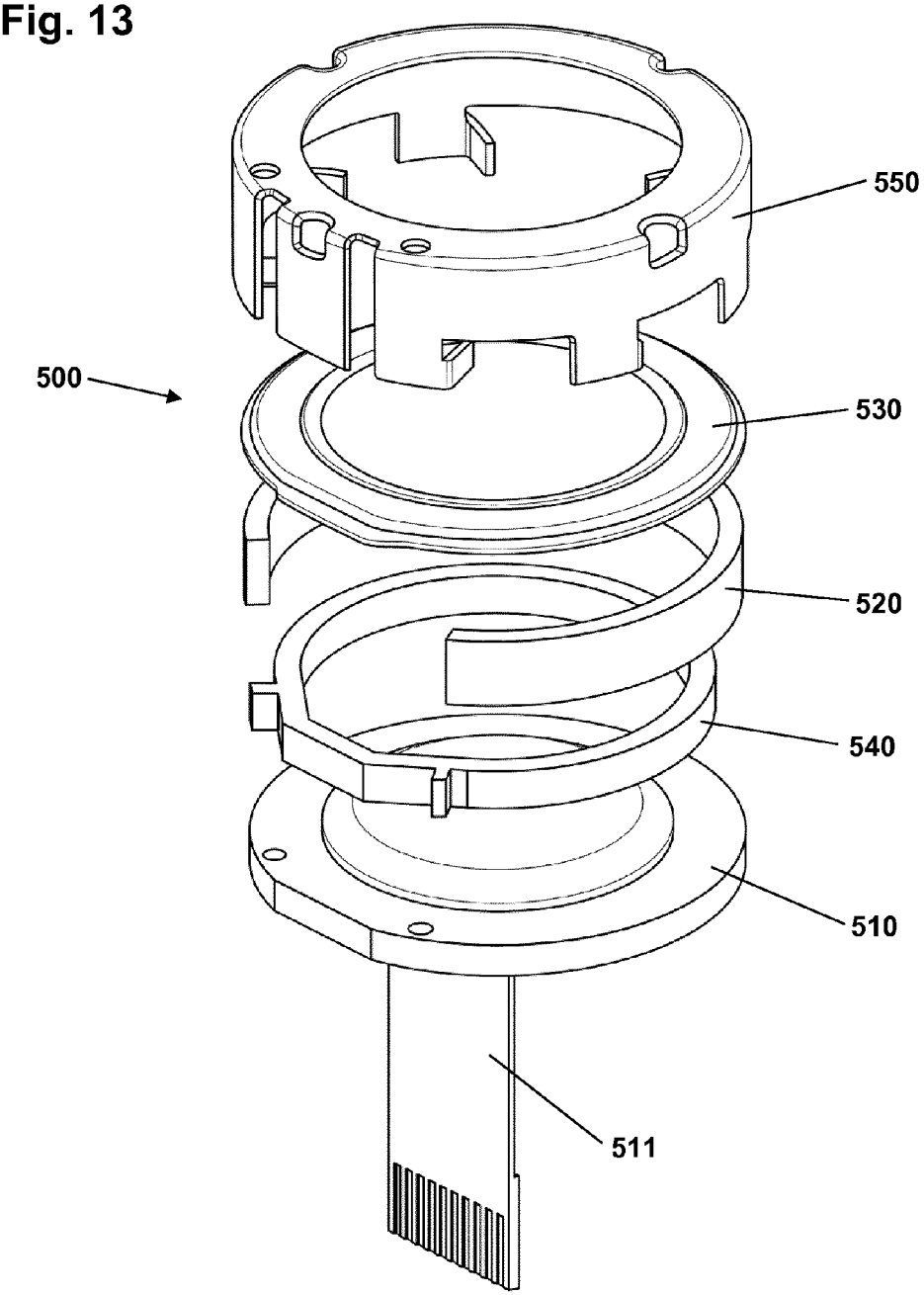
FIG. 13 shows in an exploded view a display assembly.

In the embodiment of FIG. 7 the LCD has been attached to the PCB using traditional ACF (Anisotropic Conductive Film) bonding, however, in FIG. 13 an alternative solution for attaching the LCD to a PCB is shown. More specifically, FIG. 13 shows in an exploded view a display assembly 500 comprising a PCB 510 with a flexible connector 511, a curved elastomeric connector 520 (e.g. a Zebra® connector), a segmented LCD (e.g. numeric or dot-matrix) 530, a mounting ring 540 and a housing ring 550. The LCD comprises a connector array with a plurality of connectors arranged in a first curved configuration along at a part of the curved circumferential portion, e.g. 300 degrees, and the PCB comprises a corresponding connector array having a plurality of connectors arranged in a second curved configuration corresponding at least in part to the first curved configuration. The curved elastomeric connector is adapted to establish a plurality of electrical connections between the connectors of the two connector arrays when the LCD, the PCB and the elastomeric connector is arranged in conducting contact. In an assembled state the housing ring is attached to the PCB thereby holding the remaining components into forced engagement with each other.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery device comprising:
   a housing,
   a drug-filled cartridge or structure for receiving a drug-filled cartridge, the cartridge comprising an axially displaceable piston and a distal outlet portion,
   drug expelling structure comprising:
   dose setting structure allowing a user to set a dose of drug to be expelled, the dose corresponding to a number of increments from an initial state,
   an axially displaceable piston rod adapted to move the piston of a cartridge in a distal direction to thereby expel drug from a cartridge,
   an indication member adapted to rotate in a first direction relative to the housing and corresponding to the set dose, and rotate in an opposed second direction relative to the housing and corresponding to an expelled dose, the indication member having an initial rotational position corresponding to both the initial state and the fully expelled dose state, and
   actuation structure for expelling a set dose, the drug expelling structure being in an expelling state during expelling of a dose,
   sensor structure having a synchronized state in which an incremental counter is synchronized with the rotational position of the indication member and has a reference point corresponding to the initial rotational position of the indication member, the sensor structure being adapted to detect:
   the number of rotational increments performed by the indication member in the first direction corresponding to a set dose,
   the number of rotational increments performed by the indication member in the second direction corresponding to an expelled dose,
   an expelling state for the expelling structure, and
   a non-synchronized error state,
   wherein, when a non-synchronized error state is detected, the sensor structure means is adapted to automatically re-synchronize by:
   detecting the number of rotational increments for a set dose,
   in the expelling state, detecting the number of rotational increments for a subsequent expelled dose, and
   if the two numbers of increments are the same, reset the reference point corresponding to the current rotational position of the indication member.

2. A drug delivery device as in claim 1, wherein the sensor structure is in the form of a sensor assembly comprising:
   (i) a first portion comprising a first rotary sensor part, the first rotary sensor part comprising a surface with a plurality of individual electrically conducting rotational position sensor segments arranged in a pattern,
   (ii) a second portion comprising a second rotary sensor part arranged rotationally relative to the first portion, the second rotary sensor part comprising a plurality of rotational position contact structures adapted to be in contact with conducting rotational position sensor segments on the first sensor rotary part, wherein the rotational position contact structures are configured to engage and connect different rotational position sensor segments as the first and second rotary sensor part of the sensor assembly rotate relative to each, the created connections being indicative of a rotational position between the first and second sensor assembly portions.

3. A drug delivery device as in claim 2, wherein:

the first rotary sensor part surface further comprises an electrically conducting axial position sensor segment, the second rotary sensor part further comprises an axial position contact structure adapted to be in contact with the conducting axial position sensor segment on the first rotary sensor part, the axial position contact structure comprises an axial position contact having a connected position in which the axial position contact is in contact with the axial position sensor segment, and a dis-connected position in which the axial position contact is not in contact with an axial position sensor segment, and the connected position corresponds to the expelling state, the drug delivery device further comprising actuator structure for axially moving the axial position contact between the connected and the dis-connected position.

4. A drug delivery device as in claim 3, wherein the second rotary sensor part is in the form of a metallic disc member comprising a plurality of integrally formed flexible arms forming the contact structures, at least one of the flexible arms being axially moveable to form a flexible switch arm comprising the axial position contact.

5. A drug delivery device as in claim 3, wherein:

the first portion is arranged rotationally relative to the housing, the second portion is arranged non-rotationally relative to the housing, and at least one of the first and second portions are arranged axially moveable relative to the housing, and the actuator structure is arranged between the housing and the second portion.

6. A drug delivery device as in claim 4, wherein the actuator structure is in the form of a mechanical connection formed between the housing and the flexible switch arm, whereby relative axial movement between the housing and the flexible switch arm moves the axial position contact between the connected and dis-connected positions.

7. A drug delivery device as in claim 6, wherein the first portion of the sensor assembly is mounted to and rotates with the indication member, the first portion comprising electronic circuitry adapted to estimate an amount of expelled drug based on detection of rotational movement between the first and second portions corresponding to a set and/or expelled dose.

8. A drug delivery device as in claim 6, wherein the indication member is adapted to move axially between an initial and an actuated position, the first portion of the sensor assembly being mounted to move axially with the indication member.

9. A drug delivery device as in claim 8, wherein also the second portion is mounted to move axially with the indication member.

10. A drug delivery device as in claim 6, wherein the electronic circuitry comprises logging structure adapted to create a log for dose amounts of drug expelled from a cartridge by the drug expelling structure, wherein the dose amounts are calculated based on relative rotation between the first and second rotary sensor parts during setting and/or expelling of a dose of drug.

11. A drug delivery device as in claim 6, wherein the first portion comprises a display.

12. A drug delivery device as in claim 11, wherein the display is turned off during rotation of the first portion.

13. A drug delivery device as in claim 6, wherein the electronic circuitry comprises transmitter structure adapted to transmit stored data to an external receiver.

* * * * *